US00PP28928P2

(12) United States Plant Patent
Lim

(10) Patent No.: US PP28,928 P2
(45) Date of Patent: Feb. 6, 2018

(54) ***ROSA* PLANT NAMED 'LIM10'**

(50) Latin Name: *Rosa hybrida*
Varietal Denomination: Lim10

(71) Applicant: Peter Ping Lim, Escondido, CA (US)

(72) Inventor: Peter Ping Lim, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/330,571

(22) Filed: Oct. 13, 2016

(51) Int. Cl.
*A01H 5/02* (2006.01)

(52) U.S. Cl.
USPC ..... Plt./135

(58) Field of Classification Search
USPC ..... Plt./135
See application file for complete search history.

*Primary Examiner* — Annette H Para
(74) *Attorney, Agent, or Firm* — Cassandra Bright

(57) ABSTRACT

A new and distinct hybrid tea *Rosa* cultivar named 'Lim10' is disclosed, characterized by distinctive fully double red-orange flowers with a peppery fragrance. Plants are vigorous and can be grown on their own roots. Plants are upright, flower continuously and exhibit good resistance to blackspot diseases. The new variety is a *Rosa*, normally produced as an outdoor garden or container plant.

1 Drawing Sheet

Latin name of the genus and species: *Rosa hybrida.*
Variety denomination: 'Lim10'.

BACKGROUND OF THE INVENTION

The new *Rosa* cultivar is a product of a planned breeding program conducted by the inventor, Peter Ping Lim. The objective of the breeding program was to produce vigorous new garden hybrid tea rose varieties for ornamental commercial applications. The cross resulting in this new variety was made during April of 2009.

The seed parent is the unpatented variety *Rosa* 'The Finest'. The pollen parent is the unpatented variety *Rosa* 'Orange Fire'. The new variety was selected in June of 2010 by the inventor in a group of seedlings resulting from the 2009 crossing, in a research nursery in McMinnville, Oreg.

Asexual reproduction of the new cultivar was performed by vegetative cuttings. This was first performed at a research greenhouse in McMinnville, Oreg. in June 2011 and has shown that the unique features of this cultivar are stable and reproduced true to type in more than 5 successive generations.

SUMMARY OF THE INVENTION

The cultivar 'Lim10' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Lim10' These characteristics in combination distinguish 'Lim10' as a new and distinct *Rosa* cultivar:

1. Double flowering tea rose with a vigorous plant habit.
2. Heat tolerance.
3. Continuing flowering double orange-red hybrid tea flower.
4. Deep orange-red coloration.

5. Peppery fragrance.
6. Can be grown without grafting, performs vigorously on its own roots.
7. Easy to propagate and root.
8. Resistance to black spot disease.

Plants of the new cultivar 'Lim10' are similar to plants of the seed parent, in most horticultural characteristics, however, plants of the new cultivar 'Lim10' differ in the following:

1. The seed parent has a creamy white flower, the new variety has a deep orange-red flower.

Plants of the new cultivar 'Lim10' are similar to plants of the pollen parent in most horticultural characteristics, however, plants of the new cultivar 'Lim10' differs in the following;

1. The pollen parent has orange colored flowers, the new variety has red-orange flowers.
2. The new variety is a hybrid tea rose, the pollen parent is a floribunda.

COMMERCIAL COMPARISON

Plants of the new cultivar 'Lim10' can be compared to the commercial variety *Rosa* 'Trumpeter', unpatented. These varieties are similar in most horticultural characteristics, however 'Lim10' differs in the following:

1. The flower color of the new variety is a deeper red-orange.
2. The new variety is a hybrid tea rose, this comparator is a floribunda.
3. The new variety is more heat resistant than this comparator.
4. The new variety is more resistant to black spot than this comparator.
5. The new variety is more upright in growth habit.
6. The new variety has a stronger, more peppery scent.
7. The new variety has a larger flower than this comparator.

Plants of the new cultivar 'Lim10' can also be compared to the commercial variety *Rosa* 'Orange Impressionist', U.S. Plant Pat. No. 15,738. These varieties are similar in most horticultural characteristics, however 'Lim10' differs in the following:

1. The new variety has a significantly larger flower than this comparator.
2. The comparator has a flower with a white coloration to the underside of the petal
3. The new variety is more heat resistant than this comparator.
4. The new variety is more resistant to black spot than this comparator.

BRIEF DESCRIPTION OF THE PHOTOGRAPH

The accompanying photograph in FIG. 1 illustrates in full color a close up of an individual flower. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'Lim10' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'Lim10'.

PROPAGATION

Time to initiate roots: About 15 days at approximately 20° C.

Time to produce a rooted cutting: About 35 days at approximately 20° C.

PLANT

Age of plant described: Approximately 2 years.
Growth habit: Compact spreading.
Container size: 2 gallon.
Height: 55 cm.
Plant spread: 65 cm.
Rootstock: Own root.
Growth rate: Moderate.
Branching characteristics: Sympodial branching.
Length of primary lateral branches: Average 20 cm.
Diameter of lateral branches: Approximately 5 to 7 mm.
Quantity branches: 6 to 8 main branches, moderate lateral branches, 5 to 12 lateral branches per main branch.
Branches:
Young wood:
*Diameter*.—Approximately 3 mm.
*Texture*.—Glabrous, scant thorns.
*Approximately density/quantity of thorns*.—Approximately 3 per linear cm.
*Color*.—Near Green 138D, anthocyanin at nodes only, colored near Greyed-Purple 187B.
Branches:
Old wood:
*Diameter*.—Approximately 2.0 cm.
*Color*.—Near Greyed-Green 194B.
*Texture*.—Rough thick woody striations.
Thorns:
*Approximately density/quantity of thorns*.—Approximately 5 per linear cm.
*Color of thorns*.—Immature: Greyed-Purple 187A. Mature: Near Greyed-Orange 166A.
*Shape*.—Deltoid, moderately hooked.
*Height*.—Average 5 mm.
*Diameter*.—Base near 5 mm. Tip near 0.2 cm.

FOLIAGE

Leaf:
*Arrangement*.—Alternate and compound.
*Quantity*.—Average 5 to 9 per main branch.
*Internode*.—Average range 1.3 to 4.0 cm.
*Average length*.—Approximately 9.0 cm.
*Average width*.—Approximately 6.5 cm.
Rachis:
*Average length*.—Approximately 2.5 cm.
*Average diameter*.—Approximately 0.2 cm.
*Color*.—Near RHS Yellow-Green 144B, flushed Greyed-Purple N186C.
*Texture*.—Glabrous all surfaces.
Leaflet:
*Quantity*.—3 or 5 per leaf, most commonly 5.
*Average length*.—Approximately 4.0 cm.
*Average width*.—Approximately 3.0 cm.
*Shape of blade*.—Ovate.
*Apex*.—Acute.
*Base*.—Rounded.
*Margin*.—Serrate.
*Appearance of top surface*.—Slightly glossy.
*Appearance of bottom surface*.—Matte.
*Texture of top surface*.—Glabrous.
*Texture of bottom surface*.—Glabrous.
*Color*.—Young foliage upper side: Near Yellow-Green 147A, flushed N186C. Young foliage under side: Near Yellow-Green 148A, flushed 187B, veins 187B. Mature foliage upper side: Near Green 137A. Mature foliage under side: Near Green 138B.
*Venation*.—Type: Reticulate. Venation color upper side: Near Yellow-Green 144C. Venation color under side: Near Yellow-Green 144C.
Petiole:
*Average length*.—Approximately 2.0 cm.
*Average diameter*.—Approximately 0.2 cm.
*Color*.—Near Yellow-Green 144B.
*Texture*.—Glabrous.

FLOWER

Natural flowering season: Spring until Autumn.
Inflorescence type and habit: Single occurring, fully double rotate flowers.
Rate of flower opening: Approximately 4 days from bud to fully opened flower.
Flower longevity on plant: 10 to 14 days, after fully opened.
Quantity of flowers: 10 to 20 fully opened flowers and buds.

Flower size:
*Diameter*.—Approximately 8 cm.
*Height*.—Approximately 4 cm.
Peduncle:
*Length*.—3.5 cm.
*Diameter*.—0.35 cm.
*Color*.—Near RHS Greyed-Purple 187B.
Petals:
*Petal arrangement*.—Multiple rotate, overlapping whorls.
*Petal quantity*.—50 to 60.
*Length*.—3.1 cm.
*Width*.—2.6 cm.
*Shape*.—Somewhat broad ovate.
*Margin*.—Entire, slight downward curve.
*Apex*.—Rounded, sometimes notched with age.
*Base*.—Broad attenuate.
*Texture*.—Glabrous all surfaces.
Color:
*Petals*.—When opening: Upper surface: Near RHS Red 40A, but brighter. Very small basal blotch near White 155D. Lower surface: Near RHS Red 50A, but brighter. Streaks and small basal blotch near White 155D. Fully opened: Upper surface: Near RHS Red 43B, flushed at margin 45B, base 43C. Lower surface: Near RHS Red 47B, flushed at margin 46B, base 49D. Color Changes when aging, both surfaces: Upper section near Red 45C, thin margin Greyed-Purple 187A, base 49D.
Bud:
*Shape*.—Ovate.
*Length*.—Approximately 2.3 cm.
*Diameter*.—Approximately 1.5 cm.
*Color*.—Near Red 44A.
Sepals:
*Quantity*.—5.
*Length*.—2.2 cm.
*Width*.—1.0 cm.
*Shape*.—Deltoid.
*Apex*.—Apiculate.
*Margin*.—Entire.
*Color*.—Interior Surface: Near Green RHS 138D, flushed Greyed-Purple N187C. Exterior Surface: Near Green RHS 138B flushed 187B.
*Texture*.—Densely and minutely pubescent upper and lower surfaces.
Receptacle:
*Length*.—1.0 cm.
*Width*.—1.4 cm.
*Shape*.—Flattened dome.
*Color*.—Near RHS Green 143D.
Fragrance: Distinctive peppery fragrance.

REPRODUCTIVE ORGANS

Stamens:
*Quantity*.—Average range 90 to 110.
*Filament length*.—Approximately 0.4 cm.
*Filament color*.—Near Greyed-Yellow 160B.
Anthers:
*Length*.—0.2 cm.
*Shape*.—Narrow globular.
*Color*.—Near Greyed-Orange N170A.
*Pollen*.—Color: Greyed-Orange N170A. Quantity: Scant.
Pistil:
*Number*.—Approximately 50 to 70.
*Pistil length*.—Approximately 0.8 cm.
*Style*.—Length: Approximately 0.4 cm. Color: Near Yellow 2D.
*Stigma*.—Shape: Linear. Color: Near Yellow 2D.
*Ovary color*.—Near RHS Near Yellow 2D.
*Ovary shape*.—Oblong.
*Ovary length*.—Average 0.4 cm.
*Ovary diameter*.—Average 0.2 cm.

OTHER CHARACTERISTICS

Seeds and fruits: Not observed.
Disease/pest resistance: Good overall disease resistance to normal pests and diseases typical of garden roses. Very good resistance to blackspot diseases.

What is claimed is:

1. A new and distinct hybrid tea cultivar of *Rosa* plant named 'Lim10' as herein illustrated and described.

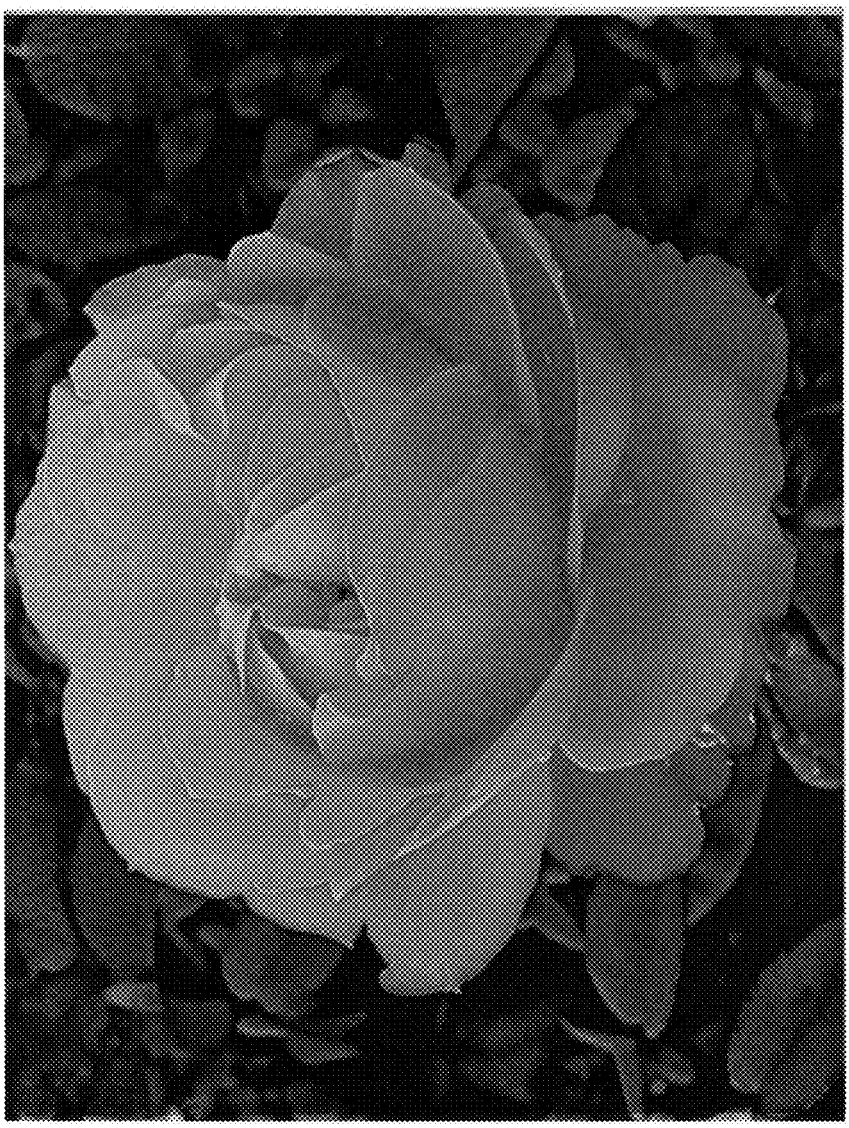

* * * * *